US011925480B2

(12) United States Patent
Liu et al.

(10) Patent No.: US 11,925,480 B2
(45) Date of Patent: Mar. 12, 2024

(54) SYSTEMS AND METHODS FOR SAMPLING AND ANALYZING THE COMMON MODE NOISE ON ELECTROCARDIOGRAM SIGNALS TO HELP MINIMIZING THE COMMON MODE INTERFERENCE TO ELECTROCARDIOGRAM SIGNALS

(71) Applicant: Drägerwerk AG & Co. KGaA, Lübeck (DE)

(72) Inventors: Lixin Liu, Brookline, MA (US); Derek Y. Qin, Andover, MA (US)

(73) Assignee: Drägerwerk AG & Co. KGaA (DE)

( * ) Notice: Subject to any disclaimer, the term of this patent is extended or adjusted under 35 U.S.C. 154(b) by 205 days.

(21) Appl. No.: 17/490,002

(22) Filed: Sep. 30, 2021

(65) Prior Publication Data

US 2022/0202337 A1 Jun. 30, 2022

Related U.S. Application Data

(60) Provisional application No. 63/131,163, filed on Dec. 28, 2020.

(51) Int. Cl.
*A61B 5/00* (2006.01)
*A61B 5/308* (2021.01)
*A61B 5/339* (2021.01)
*A61B 5/346* (2021.01)
*A61B 5/305* (2021.01)

(52) U.S. Cl.
CPC ............ *A61B 5/7203* (2013.01); *A61B 5/308* (2021.01); *A61B 5/339* (2021.01); *A61B 5/346* (2021.01); *A61B 5/7257* (2013.01); *A61B 5/305* (2021.01)

(58) Field of Classification Search
CPC ....... A61B 5/7203; A61B 5/305; A61B 5/308; A61B 5/339; A61B 5/346; A61B 5/7257; A61B 5/002
See application file for complete search history.

(56) References Cited

U.S. PATENT DOCUMENTS

| | | | |
|---|---|---|---|
| 2019/0320979 A1* | 10/2019 | Le | A61B 5/743 |
| 2020/0170528 A1* | 6/2020 | Erasala | G01R 33/421 |
| 2020/0297282 A1* | 9/2020 | Batzer | G01R 19/0023 |
| 2021/0000347 A1* | 1/2021 | Stump | A61B 5/02444 |
| 2021/0106281 A1* | 4/2021 | Tran | A61B 5/486 |
| 2021/0196139 A1* | 7/2021 | Botzer | A61B 5/7203 |

* cited by examiner

*Primary Examiner* — Catherine M Voorhees
(74) *Attorney, Agent, or Firm* — Design IP (57) ABSTRACT

Systems, computing platforms, and methods for sampling and analyzing common mode noise on electrocardiogram signals to help to minimize the interference to the electrocardiogram signals are disclosed. Exemplary implementations may: obtain electrocardiogram signals from one or more sensors configured to be attached to a patient and communicatively connected to a patient monitor; receive the electrocardiogram signals from one or more sensors by the patient monitor; display the electrocardiogram signals on one or more displays of the patient monitor; sample and analyze a direct current range and an alternating current spectrum to identify common mode interference levels within the obtained electrocardiogram signals; display the direct current range and the alternating current spectrum via the one or more displays of the patient monitor; and update the display of the direct current range and the alternating current spectrum in real time to identify sources of common mode interference.

29 Claims, 7 Drawing Sheets

| Samples per second (SPS) & Number of samples | Sample Duration each calculation | Resolution | Multiply/Second | Add/Second | Percentage of CPU horsepower @ 200MHz |
|---|---|---|---|---|---|
| 500 SPS; 1024 Samples | 2 Seconds | 0.5Hz | 5,000 | 20,000 | 0.13/1,000 |
| 500 SPS; 2024 Samples | 4 Seconds | 0.25Hz | 6,000 | 24,000 | 0.15/1,000 |
| 2,000 SPS; 1024 Samples | 0.5 Seconds | 2Hz | 20,000 | 80,000 | 0.5/1,000 |
| 2,000 SPS; 2048 Samples | 1 Second | 1Hz | 24,000 | 96,000 | 0.56/1,000 |

SYSTEMS AND METHODS FOR SAMPLING AND ANALYZING THE COMMON MODE NOISE ON ELECTROCARDIOGRAM SIGNALS TO HELP MINIMIZING THE COMMON MODE INTERFERENCE TO ELECTROCARDIOGRAM SIGNALS

FIELD OF THE DISCLOSURE

The present disclosure relates to systems, computing platforms, and methods for sampling and analyzing, for example, the common mode noise on electrocardiogram (ECG) signals to help filtering or minimizing common mode interference to the electrocardiogram signals.

BACKGROUND

Patient monitoring systems are used to measure and monitor parameters of a patient. The patient monitoring system can, for example, display information related to the measured physiological parameters of a patient including heart rate, oxygen saturation (SpO2), temperature, blood pressure, perfusion index (PI), heartbeat waveforms, end tidal carbon dioxide, and/or other physiological parameters.

Moreover, in some scenarios, patient monitoring system are comprised of two or more medical devices with a plurality of sensors working in conjunction. For example, a patient monitor may interface with a plurality of sensors (e.g., electrocardiogram electrodes, temperature sensors, blood pressure sensors, etc.) affixed to body of a patient. Likewise, there may be automated, non-invasive blood pressure measuring devices, ultrasound machines, ventilators, and anesthesia devices in close proximity to the patient. Moreover, a medical professional may use mobile computing devices (tablet, smartphones, personal digital assistants, pagers, etc.) when caring for the patient. With all of these electronic devices in close proximity, there is potential for interference (e.g., noise, crosstalk) between the various devices. This interference may cause data to become less accurate when displayed on a patient monitor, for example.

SUMMARY

Common mode interference (or noise) is one potential source of degraded performance issues of the ECG monitoring devices (e.g., patient monitors) of the patient monitoring system. The common mode noise is often generated by power line, adjacent equipment, field construction or a degraded connection. Often times, to debug the problem, field support technicians and design engineers are sent to locate and identify the causes of the interference. Additionally, there is lack of debugging tools to help the field support technicians and design engineers to identify the root cause of the interference.

The present system and methods provide tools, where a hardware circuit can provide the status of the common mode noise, and software samples and analyzes the DC (direct current) range and AC (alternating current) spectrum to identify and display a representation of the noise level the devices (e.g., ECG monitoring devices) are experiencing. Making this info readily available in a display and in real-time will benefit field support technicians and design engineers in identifying and reducing common mode noise in devices. It may also help the manufacturers to manufacture devices that emit less noise and/or filter out common mode noise. Additionally, this debugging could be implemented during the installation of the medical devices. While the systems and method described hereinbelow are directed to medical devices, one of ordinary skill in the art can appreciate how these systems and methods could be implemented in many other (e.g., non-medical) devices.

More specifically, one aspect of the present disclosure relates to a system configured for sampling and analyzing the common mode noise on electrocardiogram signals to help to minimize the interference to the electrocardiogram signals. The system may include one or more hardware processors configured by machine-readable instructions. The processor(s) may be configured to obtain electrocardiogram signals from one or more sensors configured to be attached to a patient and communicatively connected to a patient monitor. The processor(s) may be configured to receive the electrocardiogram signals from one or more sensors by the patient monitor. The processor(s) may be configured to display the electrocardiogram signals on one or more displays of the patient monitor. The processor(s) may be configured to sample and analyze a DC (direct current) level and an AC (alternating current) spectrum to identify common mode interference levels within the obtained electrocardiogram signals. The processor(s) may be configured to display the DC level and the spectrum via the one or more displays of the patient monitor. The processor(s) may be configured to update the display of the spectrum (including both DC and AC levels) in real time to identify sources of common mode interference.

In some implementations of the system, users may make changes to at least one of system configurations or system location in order to cause changes in the amount of common interference detected by the patient monitor.

In some implementations of the system, the changes in the amount of common mode interference may be reflected in direct current level and the alternating current spectrum.

In some implementations of the system, the changes in the amount and frequency of common mode interference may be indicative of causes of the common mode noise.

In some implementations of the system, identifying causes of common mode noise may further include generating and storing a knowledge base of interference causes.

In some implementations of the system, the knowledge base of interference causes may be stored in a database such that new interference measurements to be compared to previous interference causes measurements.

In some implementations of the system, sampling and analyzing a direct current range and an alternating current spectrum to identify common mode interference levels may include fast Fourier transformation-based spectrum analysis.

Another aspect of the present disclosure relates to a computing platform configured for sampling and analyzing common mode noise on electrocardiogram signals to enable filtering of common mode interference of the electrocardiogram signals. The computing platform may include a non-transient computer-readable storage medium having executable instructions embodied thereon. The computing platform may include one or more hardware processors configured to execute the instructions. The processor(s) may execute the instructions to obtain electrocardiogram signals from one or more sensors configured to be attached to a patient and communicatively connected to a patient monitor. The processor(s) may execute the instructions to receive the electrocardiogram signals from one or more sensors by the patient monitor. The processor(s) may execute the instructions to display the electrocardiogram signals on one or more displays of the patient monitor. The processor(s) may execute the instructions to sample and analyze a direct current range and an alternating current spectrum to identify common mode interference levels within the obtained electrocardiogram signals. The processor(s) may execute the instructions to display the spectrum of the common mode noise via the one or more displays of the patient monitor. The processor(s) may execute the instructions to update the display of the direct current level and the alternating current spectrum in real time to identify sources of common mode interference.

Yet another aspect of the present disclosure relates to a method for sampling and analyzing the common mode noise on electrocardiogram signals to help to minimize the interference to the electrocardiogram signals. The method may include obtaining electrocardiogram signals from one or more sensors configured to be attached to a patient and communicatively connected to a patient monitor. The method may include receiving the electrocardiogram signals from one or more sensors by the patient monitor. The method may include displaying the electrocardiogram signals on one or more displays of the patient monitor. The method may include sampling and analyzing a direct current range and an alternating current spectrum to identify common mode interference levels within the obtained electrocardiogram signals. The method may include displaying the direct current range and the alternating current spectrum via the one or more displays of the patient monitor. The method may include updating the display of the direct current range and the alternating current spectrum in real time to identify sources of common mode interference.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

In the following, details are set forth to provide a more thorough explanation of the embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise. For example, variations or modifications described with respect to one of the embodiments may also be applicable to other embodiments unless noted to the contrary.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Directional terminology, such as "top", "bottom", "below", "above", "front", "behind", "back", "leading", "trailing", etc., may be used with reference to the orientation of the figures being described. Because parts of embodiments can be positioned in a number of different orientations, the directional terminology is used for purposes of illustration. It is to be understood that other embodiments may be utilized and structural or logical changes may be made without departing from the scope defined by the claims. The following detailed description, therefore, is not to be taken in a limiting sense. Directional terminology used in the claims may aid in defining one element's spatial or positional relation to another element or feature, without being limited to a specific orientation.

In general, a tool for measuring and identifying causes of common mode noise (or "CM" noise), which ECG monitoring devices may experience are not readily available. Additionally, the amount and frequency range of the noise can vary significantly with different hospitals, operating room settings (e.g., which devices are implemented and where they are located), patient (e.g., which medical devices are connected to the patient and on how), and electrode condition. There is a lack of tools to debug common mode noise related issues. In general, the present system and methods are is directed to in-system electrocardiogram (ECG) common mode interference monitoring and filtering to identify and debug common mode noise related issues. Making the CM noise spectrum readily displayed on an ECG monitor in real time will help to debug and solve noise related issues in the field, and help understand hospital noise environment quantitatively. More specifically, the present system and methods sample and displays in real time without interrupting ECG operation, and provides information to improve post ECG signal processing.

Figure 1:
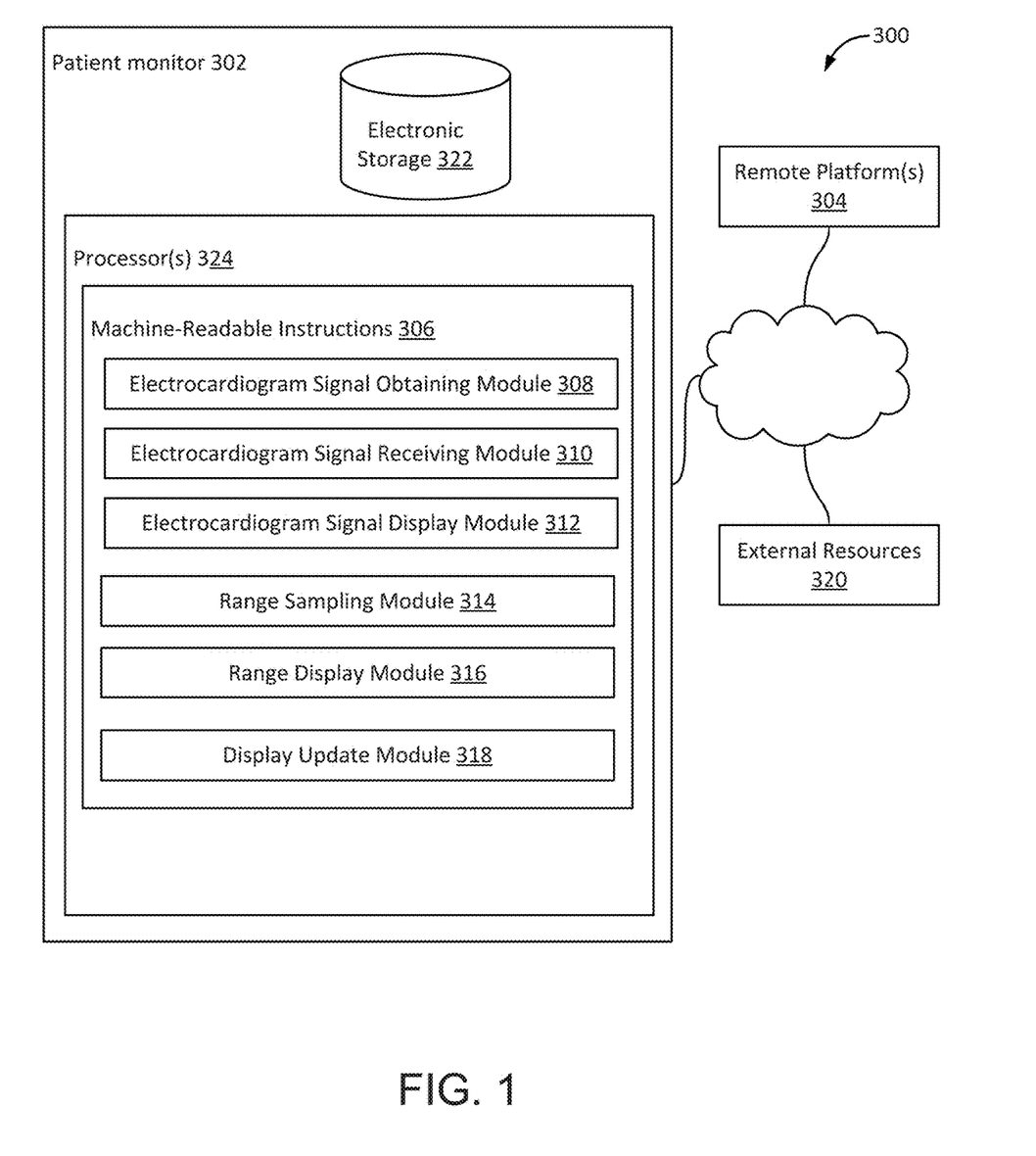
FIG. 1 illustrates a system configured for sampling and analyzing common mode noise on electrocardiogram signals to help to minimize the interference to the electrocardiogram signals, in accordance with one or more implementations.

FIG. 1 is a block diagram that illustrates a system 300 configured for sampling and analyzing common mode noise in electrocardiogram signals to help to minimize and/or eliminate the unwanted interference (e.g., common mode noise) in the electrocardiogram signals, in accordance with one or more implementations. This system (300a to 300n) could reside on one or more medical devices (e.g., patient monitor 302, 3$^{rd}$ party devices 102a, current devices 102b, legacy devices 102c, or may resides in the backend 250, for example, as detailed below in FIGS. 6 and 7). Alternatively, this system could be implemented on a computing device such as a laptop, tablet, smartphone, and/or personal digital assistant (PDA), to list a few examples. In yet another embodiment, it could be stored in a centralized storage location (e.g. a server, or cloud-based storage medium) and accessed via a wired or wireless connection with the centralized storage location.

In some implementations, system 300 may be comprised of one or more patient monitors 302 (e.g., medical devices 102a-102c). Patient monitor 302 may be configured to communicate with one or more remote platforms according to a client/server architecture, a peer-to-peer architecture, and/or other architectures. Remote platform(s) 304 may be configured to communicate with other remote platforms via patient monitor 302 and/or according to a client/server architecture, a peer-to-peer architecture, and/or other architectures. Users may access system 300 via patient monitor 302 and/or remote platform(s) 304.

Patient monitor 302 may be configured by machine-readable instructions 306. Machine-readable instructions 306 (e.g., such as software or firmware) may include one or more instruction modules. The instruction modules may include computer program modules (detailed hereinbelow). The instruction modules may include one or more of electrocardiogram signal obtaining module 308, electrocardiogram signal receiving module 310, electrocardiogram signal display module 312, range sampling module 314, range display module 316, display update module 318, and/or other instruction modules.

Electrocardiogram signal obtaining module 308 of the machine-readable instructions 306 may be configured to obtain electrocardiogram signals from one or more sensors configured to be attached to a patient and communicatively connected to, for example, a patient monitor (e.g., one of the medical devices 102a-102c). As is detailed herein, users may make changes to at least one of system configurations and system (e.g., device location) locations in order to cause changes in the amount of common mode interference detected by the patient monitor. The changes in the amount of common mode interference may be indicative of causes of the common mode noise. Identifying causes of common mode noise may further include generating and storing a knowledge base of interference causes. The knowledge base of interference causes may be stored in a database such that new interference measurements to be compared to previous interference causes measurements.

Electrocardiogram signal receiving module 310 may be configured to receive the electrocardiogram signals from one or more sensors by the patient monitor. This module may perform pre/post processing of the signal to reduce or remove other types of noise in the signals. Electrocardiogram signal display module 312 may be configured to display the electrocardiogram signals on one or more displays of the patient monitor (as detailed in FIG. 4). The displayed information provides a visual indication of the noise in real-time. Display update module 318 may be configured to update the display of the direct current range and the alternating current spectrum in real time to identify sources of common mode interference in a display or graphical user interface. As detailed hereinbelow, the GUI could be displayed on medical devices (e.g., 102a-102c) or on a portable computing device such as a laptop, tablet, smartphone, to list a few examples.

In some implementations, sampling and analyzing a direct current range and an alternating current spectrum to identify common mode interference levels may include fast Fourier transformation-based spectrum analysis. As detailed in FIG. 5, in some implementations, the fast Fourier transformation may include a 1024 points fast Fourier transformation analysis. In some implementations, the fast Fourier transformation may include a 2048 points fast Fourier transformation analysis. Increased data points may provide additional precision and/or accuracy, but will require additional computing resources. Thus, the number of data points may be user definable. In some implementations, by way of non-limiting example, the common mode noise is a combined effect of one or more of a source voltage, a coupling scheme, and an electrode impedance. In some implementations, by way of non-limiting example, the filtering of the electrocardiogram signal may further include implementing at least of a low pass filter, highpass filter, bandpass filter, bandstop filter, notch filter, and a comb filter.

In some implementations, the filtering of the electrocardiogram signal may be performed by a processor. In some implementations, the processor may include at least one of a central processing unit digital signal processor, application-specific integrated circuit and field-programmable gate array. In some implementations, the sensors may be ECG electrodes.

In some implementations, patient monitor 302, remote platform(s) 304, and/or external resources 320 may be operatively linked via one or more electronic communication links. For example, such electronic communication links may be established, at least in part, via a network such as the Internet and/or other wired or wireless networks (e.g., internal corporate network, hospital network, etc.). It will be appreciated that this is not intended to be limiting, and that the scope of this disclosure includes implementations in which patient monitor 302, remote platform(s) 304, and/or external resources 320 may be operatively linked via some other communication media (e.g., 3G, 4G, 5G networks, ad-hoc or mesh networks, for example).

A given remote platform 304 may include one or more processors configured to execute computer program modules. The computer program modules may be configured to enable an expert or user associated with the given remote platform 304 to interface with front end 200 and/or external resources 320, and/or provide other functionality attributed herein to remote platform(s) 304. By way of non-limiting example, a given remote platform 304 and/or a given computing platform may include one or more of a server, a desktop computer, a laptop computer, a handheld computer, a tablet computing platform, a netbook, a smartphone, and/or other computing platforms.

External resources 320 may include sources of information outside of system 300, external entities participating with system 300, and/or other resources. In some implementations, some or all of the functionality attributed herein to external resources 320 may be provided by resources included in system 300.

Patient monitor 302 may include electronic storage 322, one or more processor(s) 324, and/or other components. Patient monitor 302 may include communication lines, or ports to enable the exchange of information with a network and/or other computing platforms. Illustration of patient monitor 302 in FIG. 1 is not intended to be limiting. Patient monitor 302 may include a plurality of hardware, software, and/or firmware components operating together to provide the functionality attributed herein to patient monitor 302. For example, patient monitor 302 may be implemented by a cloud of computing platforms operating together as patient monitor 302.

Electronic storage 322 may comprise non-transitory storage media that electronically stores information. The electronic storage media of electronic storage 322 may include one or both of system storage that is provided integrally (e.g., substantially non-removable) with patient monitor 302 and/or removable storage that is removably connectable to patient monitor 302 via, for example, a port (e.g., a USB port, a firewire port, etc.) or a drive (e.g., a disk drive, etc.). Electronic storage 322 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 322 may include one or more virtual storage resources (e.g., cloud storage, a virtual private network, and/or other virtual storage resources). Electronic storage 322 may store software algorithms, information determined by processor(s) 324, information received from patient monitor 302, information received from remote platform(s) 304, and/or other information that enables patient monitor 302 to function as described herein.

Processor(s) 324 may be configured to provide information processing capabilities in patient monitor 302. As such, processor(s) 324 may include one or more of a digital processor, an analog processor, a digital circuit designed to process information, an analog circuit designed to process information, a state machine, and/or other mechanisms for electronically processing information. Although processor(s) 324 is shown in FIG. 1 as a single entity, this is for illustrative purposes only. In some implementations, processor(s) 324 may include a plurality of processing units. These processing units may be physically located within the same device, or processor(s) 324 may represent processing functionality of a plurality of devices operating in coordination. Processor(s) 324 may be configured to execute modules 308, 310, 312, and/or 318, and/or other modules. Processor(s) 324 may be configured to execute modules 308, 310, 312, and/or 318, and/or other modules by software; hardware; firmware; some combination of software, hardware, and/or firmware; and/or other mechanisms for configuring processing capabilities on processor(s) 324. As used herein, the term "module" may refer to any component or set of components that perform the functionality attributed to the module. This may include one or more physical processors during execution of processor readable instructions, the processor readable instructions, circuitry, hardware, storage media, or any other components.

It should be appreciated that although modules 308, 310, 312, and/or 318 are illustrated in FIG. 1 as being implemented within a single processing unit, in implementations in which processor(s) 324 includes multiple processing units, one or more of modules 308, 310, 312, and/or 318 may be implemented remotely from the other modules. The description of the functionality provided by the different modules 308, 310, 312, and/or 318 described below is for illustrative purposes, and is not intended to be limiting, as any of modules 308, 310, 312, and/or 318 may provide more or less functionality than is described. For example, one or more of modules 308, 310, 312, and/or 318 may be eliminated, and some or all of its functionality may be provided by other ones of modules 308, 310, 312, and/or 318. As another example, processor(s) 324 may be configured to execute one or more additional modules that may perform some or all of the functionality attributed below to one of modules 308, 310, 312, and/or 318.

Figure 2:
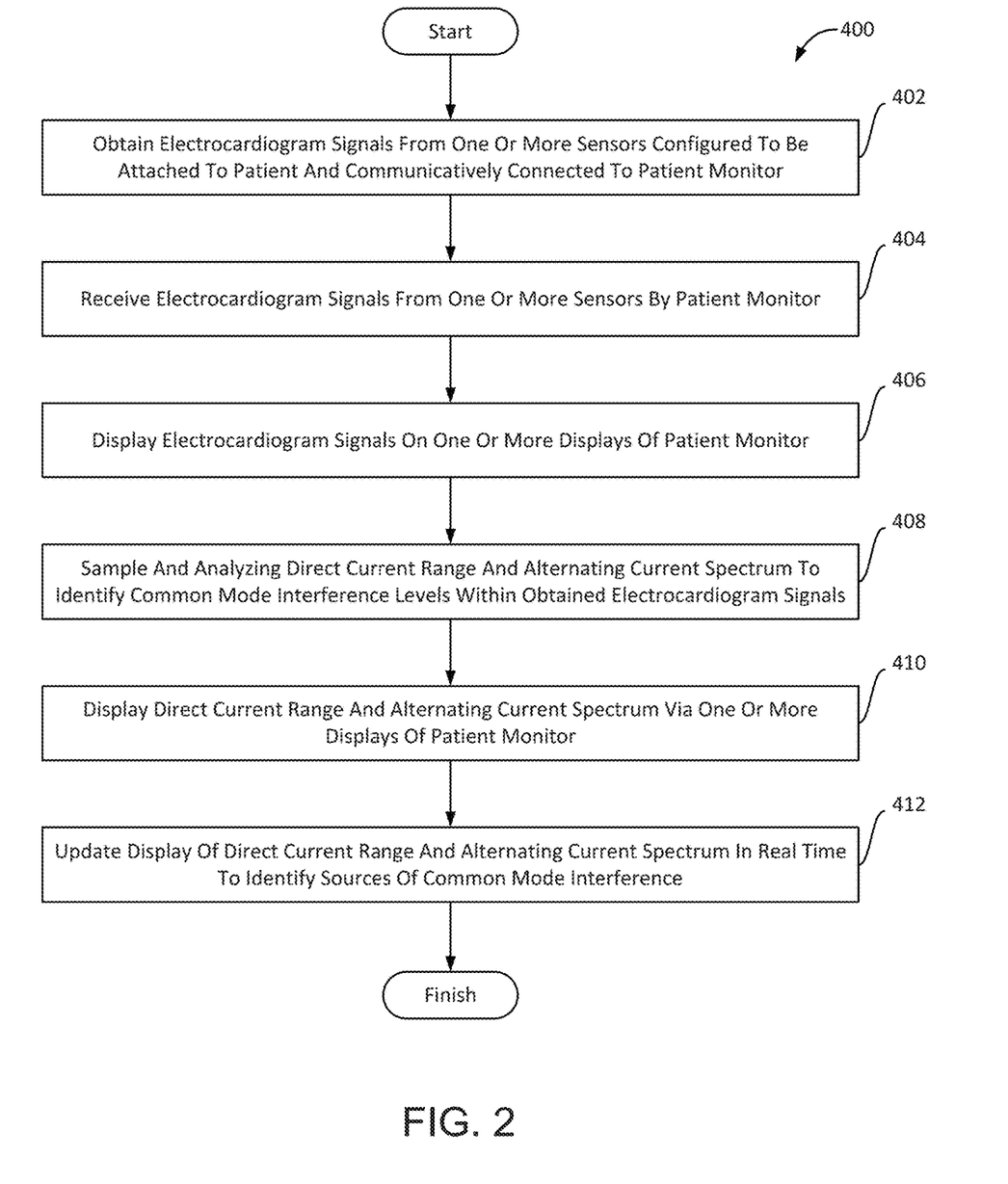
FIG. 2 illustrates a method for sampling and analyzing electrocardiogram signals to enable filtering of common mode interference of the electrocardiogram signals, in accordance with one or more implementations.

FIG. 2 illustrates a method 400 for sampling and analyzing common mode noise in electrocardiogram signals to help to minimize and/or eliminate the interference to the electrocardiogram signals, in accordance with one or more implementations. The operations of method 400 presented below are intended to be illustrative. For example, the steps described hereinbelow are described with respect to a patient monitor. However, the steps could be performed on personal computing device such as a laptop, tablet, or smartphone). In some implementations, method 400 may be accomplished with one or more additional operations not described, and/or without one or more of the operations discussed. Additionally, the order in which the operations of method 400 are illustrated in FIG. 2 and described below is not intended to be limiting.

In some implementations, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

An operation 402 may include obtaining electrocardiogram signals from one or more sensors configured to be attached to a patient and communicatively connected to a patient monitor. Operation 402 may be performed by one or more hardware processors configured by machine-readable instructions including a module that is the same as or similar to electrocardiogram signal obtaining module 308, in accordance with one or more implementations.

An operation 404 may include receiving the electrocardiogram signals from the one or more sensors by the patient monitor. Operation 404 may be performed by one or more hardware processors configured by machine-readable instructions including a module that is the same as or similar to electrocardiogram signal receiving module 310, in accordance with one or more implementations.

An operation 406 may include displaying the electrocardiogram signals on one or more displays of the patient monitor. Operation 406 may be performed by one or more hardware processors configured by machine-readable instructions including a module that is the same as or similar to electrocardiogram signal display module 312, in accordance with one or more implementations. Additionally, while not illustrated, obtained signals may also be saved into a storage device for later viewing, analysis, or for generation of reports.

An operation 408 may include sampling and analyzing a direct current range and/or an alternating current spectrum to identify common mode interference levels within the obtained ECG signals. The measurement point is at the right leg drive circuit output, V×0 shown in FIG. 3, rather than directly from the ECG signals. Operation 408 may be performed by one or more hardware processors configured by machine-readable instructions including a module that is the same as or similar to range sampling module 314, in accordance with one or more implementations.

An operation 410 may include displaying the direct current range and the alternating current spectrum via the one or more displays of the patient monitor. Operation 410 may be performed by one or more hardware processors configured by machine-readable instructions including a module that is the same as or similar to range display module 316, in accordance with one or more implementations.

An operation 412 may include updating the display of the direct current range and the alternating current spectrum in real time to identify sources of common mode interference. Operation 412 may be performed by one or more hardware processors configured by machine-readable instructions including a module that is the same as or similar to display update module 318, in accordance with one or more implementations.

Figure 3:
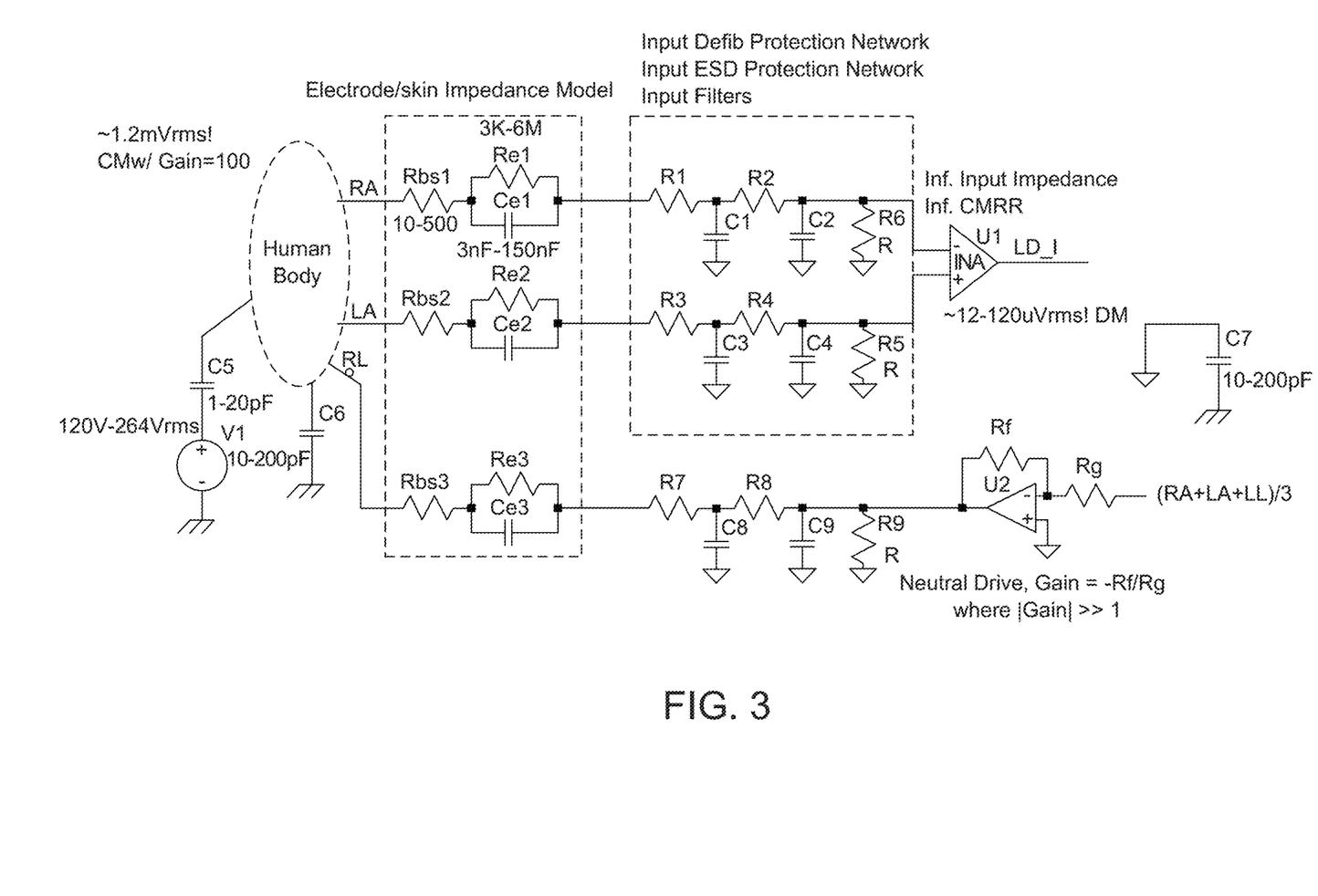
FIG. 3 illustrates a circuit diagram illustrating one exemplary circuit of right leg drive solution for common mode interference monitoring and filtering, in accordance with one or more implementations.

FIG. 3 is a circuit diagram illustrating one exemplary circuit of a right leg drive solution, from which the information is extracted for common mode interference monitoring, in accordance with one or more implementations. In more detail, the right leg drive circuit is to drive patient voltage, the average of the limb voltages, to the same level as the ECG floating ground's, so that differential amplifiers can measure the ECG lead voltages.

As illustrated in the circuit diagram, a human body connected to a plurality of ECG electrodes, labeled as RA, LA, and RL, which are part of a three-lead electrode for Right Arm (RA), Left Arm (LA), and Right Leg (RL). In the illustrated example, the human Body measures approximately 1.2 millivolts RMS (Root Mean Square) and the common mode with gain equals 100 (40 dB). Connected to the human body are a plurality of resistors and capacitors, in accordance with one embodiment. Typical ranges for the resistors and capacitors are illustrated. These components are identified as the electrode/skin impedance model and are communicatively coupled to the "human body" as illustrated.

Connected to the Right Arm and Left Arm portion of the electrode/skin impedance model are an input defib protection network, input ESD (electrostatic discharge) protection network, and input filters (as identified in the figure). This network is then connected to a differential amplifier with relatively high common mode rejection ratio (CMRR). Ideally, the differential amplifier would have infinite common mode rejection ratio, however this is typically not achievable in real-world application.

Returning to the neutral drive circuit model, the voltage of the probing point, V×0, represents the overall common mode noise experienced by the monitor due to a noise source voltage, coupling scheme, and electrode impedance.

The voltage of the probing point is sampled, and its spectrum is then displayed in a waveform, as further detailed in FIG. 4 below.

Figure 4:
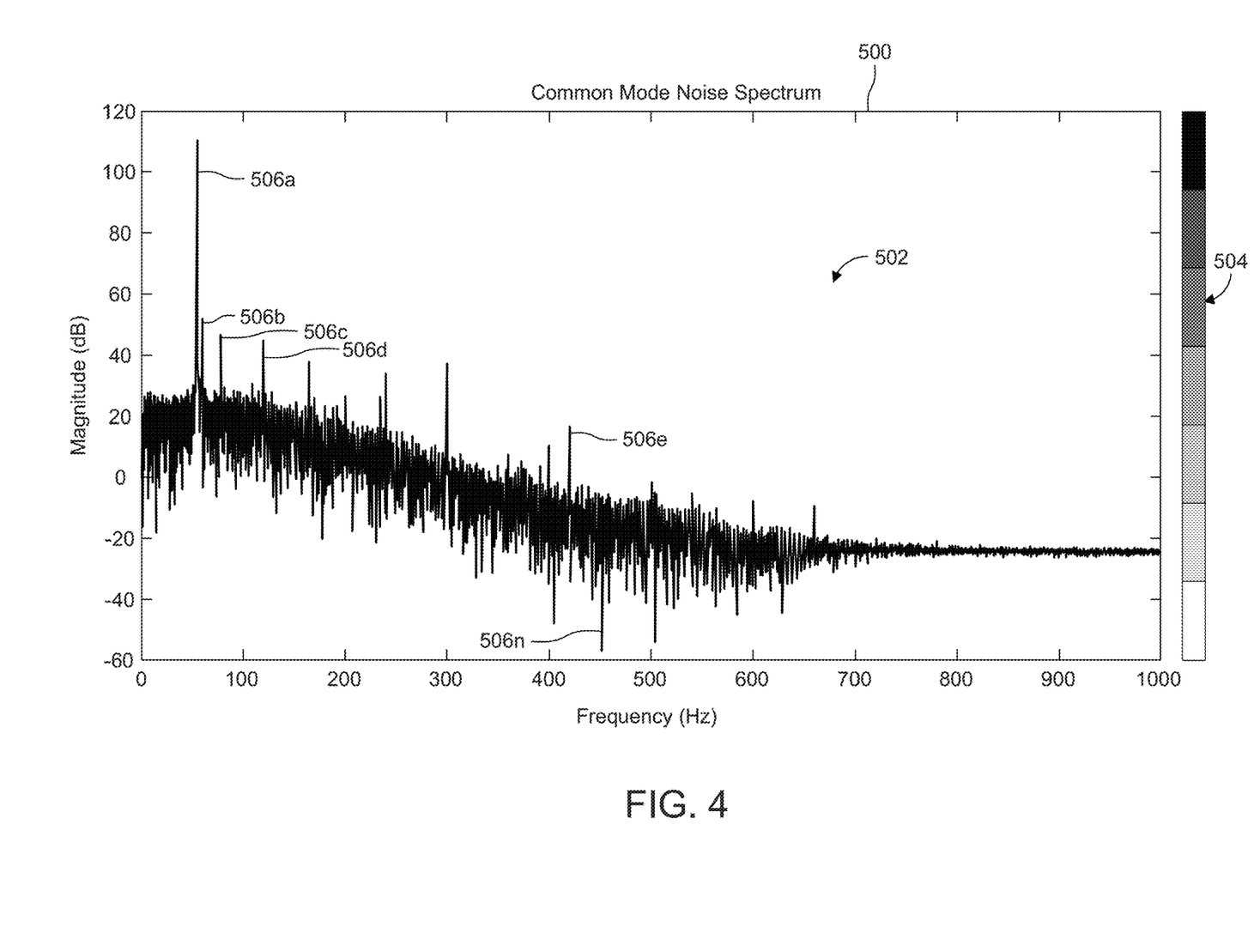
FIG. 4 illustrates a typical common mode interference spectrum and noise level indication.

FIG. 4 illustrates an exemplary output 500 that might be displayed in real-time to a user, in accordance with one embodiment. In the illustrated embodiment, the output could be displayed on one or more medical devices (e.g., $3^{rd}$ party devices 102a, current devices 102b, legacy devices 102c, the personal computer 54, or user interface 102i, detailed hereinbelow). Additionally, or alternatively, the output could be displayed on a personal computing device such as tablet or smartphone, for example.

As illustrated, the output currently being displayed is a common mode noise spectrum 502. As labeled in the figure, the X-axis is a measure of frequency and the Y-axis is a measure of magnitude in decibels (dB). Accordingly, the common mode noise spectrum 502 illustrates the magnitude and frequency of the noise being measured. While this figure is only a screenshot, in operation, the common mode noise spectrum 502 would be updating dynamically and in real-time in response to the various common mode noise being measured. Numerals 506a, 506b, 506c, 506d, 506e etc. (through 506n) illustrate some of the various peaks in the common mode noise spectrum 502. In general, each peak represents a common mode noise component at a corresponding frequency (that should be reduced or eliminated).

Additionally, in some embodiments, the common mode noise spectrum 502 and the various peaks (e.g., 506a through 506n) could be color coded with a color 504 to identify when the peaks have exceeded a predefined magnitude above a threshold (e.g., 20 dB, 40 dB, 60 dB, 80 dB, and/or 100 dB). In the illustrated embodiment, a color-coding chart goes from white to black, and utilizes a grayscale to signify various magnitudes. In an alternative embodiment, various other colors (e.g., red, orange, yellow, green, blue, etc.) could be implemented in the color coding. In yet another embodiment, color coding could be implemented to identify peaks that are either too high (e.g., exceed a predefined positive magnitude) or too low, (e.g., peaks that exceed a predefined negative threshold). This color coding would provide quick reference to peaks hat have exceed a predefined threshold.

As detailed previously, the common mode noise spectrum and peaks are updating in real time, Accordingly, the color-coding of the waveforms would also update in real time. While not illustrated, one or more buttons could be included to record "snapshots" or "screenshots" to capture a particular waveform and store that information into memory for later viewing or analysis.

Figure 5:
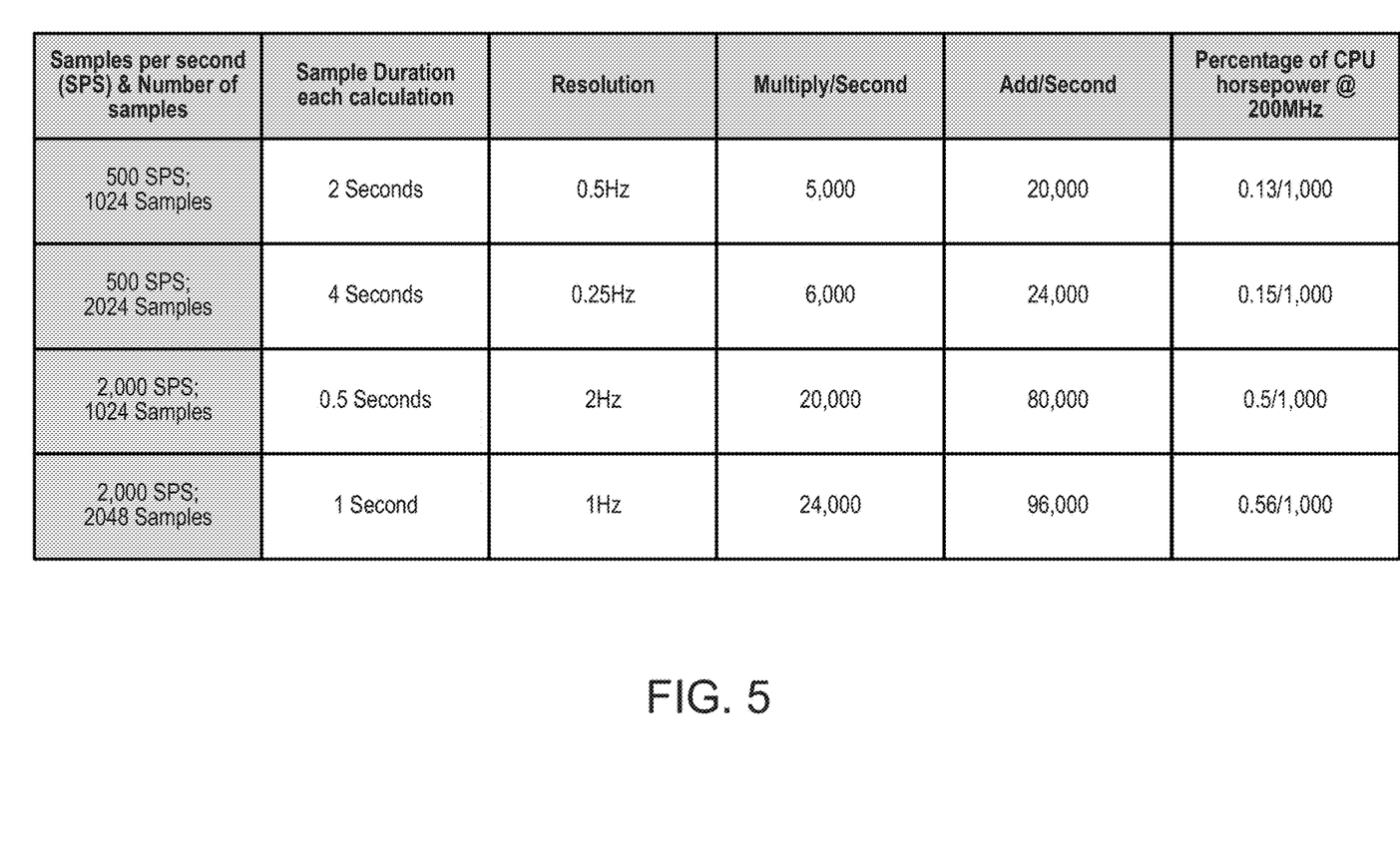
FIG. 5 illustrates a table illustrating Fast-Fourier Transform calculations resource analysis, in accordance with one or more implementations.

FIG. 5 is a table illustrating Fast-Fourier Transform calculations and a general resource analysis, in accordance with one or more implementations. That is, this chart illustrates the amount of computing power required to perform the calculations needed to generate the real-time display. Depending on the number of samples, the duration of the sample, and overall sampling rate, the output will become more accurate with additional samples and more frequent sampling. However, this additional sampling rate and number of samples requires the use of greater system resources (e.g., processor RAM, cache). Obviously, more samples and a higher sampling rate require more resources, while fewer samples and a lower sampling rate will require fewer system resources. It should be noted, however, that different devices will have different resource availability. Accordingly, the correct duration, sampling rate, and number of samples with vary depending on the device.

For example, newer devices often have multiple processors, larger caches on the processor, wider buses, more RAM (random access memory) and may communicate over faster input/output interfaces. Thus, for some devices, 1024 samples at a rate of 500 samples per second may consume a relatively larger portion of the device's resources. Conversely, for a newer device, 2048 samples at a rate of 2,000 samples per second, may represent a smaller (or insignificant) portion of the newer devices resources. As illustrated, the calculations in the illustrated table were performed on a device with a 200 megahertz (MHz) CPU. Care should be taken by the technicians to account for processor horsepower and system resources when selecting a number of samples and rate. Furthermore, this table does provide an indication of other resources required to actually process and display the data.

Alternatively, software could be programmed to analyze the resources of the system, on which the software or program is installed, and then select appropriate numbers of samples, duration, and sampling rate. In this scenario, there may be an option for user override.

As illustrated, various samples rates were tested (e.g., 500 samplers per second and 1024 samples, 500 samplers per second and 2048 samples, 2,000 samplers per second, 1024 samples, and 2,000 samplers per second, 2048 samples. Additionally, the last column illustrates percentage of CPU usage required to performs the calculations (assuming a 200 MHz CPU). As shown, the computational requirements are relatively minimal, which indicate that this process can be performed in conjunction with other CPU processes. Additionally, or alternatively, the software required to perform these calculations can be included within the devices themselves. For example, the tool could be implemented as a debugging tool, that is only accessible by technicians with administrative or superuser access to troubleshooting debugging tools that typical users would not be able to access.

Figure 6:
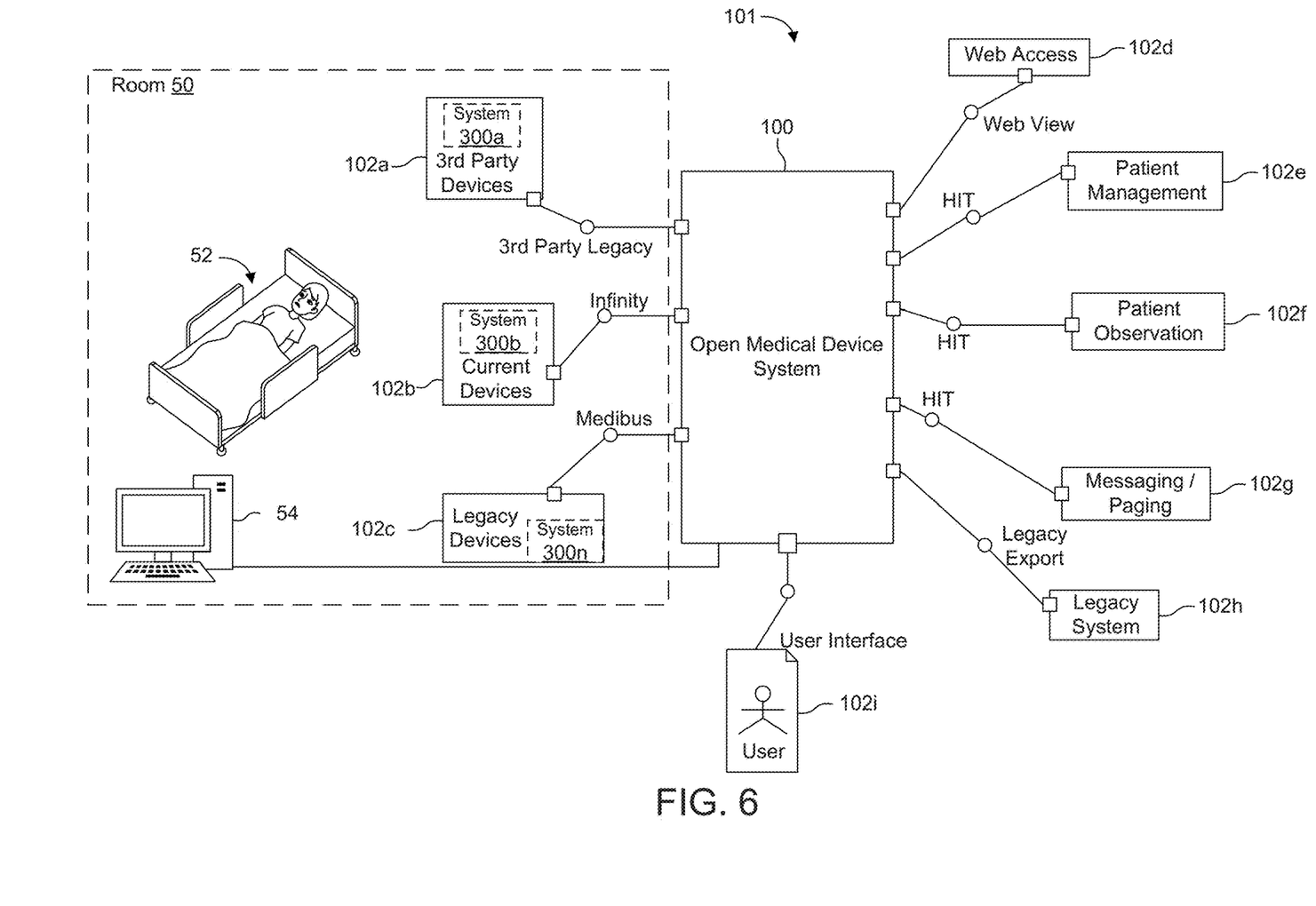
FIG. 6 is a block diagram illustrating an example open medical device system and peripheral network in which one or more disclosed embodiments may be implemented.

FIG. 6 is a diagram illustrating an example of an open medical device system 100 and peripheral network 101 in which one or more disclosed embodiments may be implemented. This figure illustrates an exemplary hospital configuration and show a plurality of electronic devices, which are often utilized during patient, and may be a source of common mode interference.

The open medical device system 100 includes a point-of-care medical device communications system that provides interconnection and interoperability of medical devices and computerized healthcare information systems. As detailed below, this includes the various point-of-care (PoC) medical devices 120a-c, which are connected to the open medical device system 100 and include a broad range of clinical monitoring, diagnostic, and therapeutic equipment. This open medical device system 100, with its numerous medical devices may reside in a patient room 50, which may include a room in a hospital or other locations where medical services may be provided (e.g., operating room, emergency room, operating room, triage area, recovery room, surgery preparation room, an intensive care room), a medical office or clinic, med-flight plane or helicopter, an ambulance, or doctors' offices, to list a few examples. A patient 52 may be situated on a bed or examination table, for example. Likewise, a terminal or personal computer 54 may also be in the room to allow the medical professional to access an EMR (Electronic Medical Record) system via a wired or wireless connection. A display/GUI for displaying various patient data and hospital or patient care information may be displayed on the personal computer 54. The display/GUI (graphical user interface) includes, but is not limited to, a keyboard, a liquid crystal display (LCD), cathode ray tube (CRT), thin film transistor (TFT), light-emitting diode (LED), high definition (HD) or other similar display device with touch screen capabilities. The patient information displayed can, for example, relate to the measured physiological parameters of the patient (e.g., blood pressure, heart related information, pulse oximetry, respiration information, etc.) as well as information related to the transporting of the patient (e.g., transport indicators).

Computerized healthcare information systems similarly include a broad range of clinical data management systems, patient care systems, and patient-based information systems. Both the point-of-care medical devices and the computerized healthcare information systems may be connected by one or more types of communication interfaces using one or more communication protocols over cable, optical connections, via wireless connections, or other means as enabled in one or more communication standards (e.g., 3G, 4G, 5G mobile networks).

The open medical device system 100 has a flexible system architecture for patient monitoring and information management over a network of devices. One or more system components may be coupled and decoupled from the system and, in some cases, exchangeable via one or more system interfaces. Each system component may extend the functionality of one or more aspects of the system as a whole. Specific system components may or may not be present depending on application of use, patient care environment, and type of patient care being provided. Thus, the system is adaptable to a multitude of configurations such that system functionality can be adapted based on the system components incorporated therewith.

Accordingly, the system architecture enables the assimilation of various system components that are capable of communicating and interacting with one or more other system components through each component's public interface. One or more system components may communicate or interact over a communication network.

System components may include hardware, software, or a combination thereof, such as in the case of firmware. Software stored in a memory device may be configured to provide an appropriate set of instructions and/or functions for specified tasks, and a programmable hardware device may execute a method according the received set of instructions and/or functions. The memory can be a single memory or one or more memories or memory locations that include, but are not limited to, a random access memory (RAM), a memory buffer, a hard drive, a database, an erasable programmable read only memory (EPROM), an electrically erasable programmable read only memory (EEPROM), a read only memory (ROM), a flash memory, hard disk or any other various layers of memory hierarchy. The memory can be used to store any type of instructions and patient data associated with algorithms, processes, or operations for controlling the general functions and operations of the physiological monitoring device.

The open medical device system 100 may be a multiple access system that provides content, such as monitoring data, diagnostic data, therapeutic data, medical records data, medical facility data, medical staffing data, messaging, etc. to multiple users. The open medical device system 100 includes a communication system that may enable multiple users to access such content through the sharing of system resources, including communication networks and bandwidth. For example, the open medical device system 100 may employ one or more communication or network protocols, such as IEEE 11073 service-oriented device connectivity (SDC), Intelligent Patient Front End (IPFE), Health Level Seven or HL7 (e.g., HL7v2 253 (in FIG. 7)), HL7 Fast Healthcare Interoperability Resources (FHIR), and the like.

IEEE 11073 SDC (hereinafter, "SDC") is a communication protocol for PoC medical devices. The SDC communication protocol includes a family of protocols, including IEEE 11073-20702, called Medical Devices Communication Profile for Web Services, a Domain Information and Service Model (IEEE 11073-10207), and Architecture and Binding definition (IEEE 11073-20701). Its primary purpose is to enable manufacturer-independent medical device-to-device interoperability. Furthermore, interconnection between medical devices and medical information systems is enabled. One or more devices, hardware, or software of the open medical device system 100 is characterized by having an SDC interface intended to communicate with other SDC devices over an IT network. Depending on its intended use, an SDC device may be approved as a medical device.

An IPFE device, in some instances also referred to as a pod, provides physiological measurements to one or more monitoring devices. When combined with one or more sensors, an IPFE device comprises a physiological patient parameter delivery system. IPFE devices may be used to measure the state of anesthesia, for example, using electrical stimulation, measure brain electrical activity such as in the case of a electroencephalogram (EEG), measure blood oxygen saturation fraction from absorption of light at different wavelengths as it passes through a finger, measure a CO2 level and/or other gas levels in an exhalation stream using infrared spectroscopy, measure oxygen saturation on the surface of the brain or other regions, measure cardiac output from invasive blood pressure and temperature measurements, measure oxygen and anesthetic agent concentrations in a stream of gas to be inhaled by a patient, measures induced electrical potentials over the cortex of the brain, measure blood oxygen saturation from an optical sensor coupled by fiber to the tip of a catheter, and/or measure blood characteristics using absorption of light. Additionally, the sensors may measure one or more of, an electrocardiogram (ECG), non-invasive peripheral oxygen saturation (SpO2), non-invasive blood pressure (NI BP), temperature, and/or tidal carbon dioxide (etCO2), apnea detection, and other similar physiological data.

In addition, IPFE devices may perform calibration processes, apply algorithms for data analysis, and identify alarm states. An IPFE device communicates with the clinical user through a host device, such as a monitoring device or therapy device that has a user interface such as a screen, a touch interface, a mouse, a keyboard, or the like. The interface between an IPFE device and its host device follows an IPFE communication protocol. Lower levels of the IPFE communication may use a Universal Serial Bus (USB) communication protocol that enables a hub structure, detection of attached devices, and a means of controlling power to each IPFE device.

The IPFE communication protocol is modeled on the SDC protocol and enables communication between an IPFE device and a monitoring or therapy device configured to monitor and/or display IPFE data generated by the IPFE device. Additionally, one monitoring or therapy device may transmit IPFE data using the IPFE communication protocol to another monitoring or therapy device. IPFE compatible devices may be connected and communicate via an IPFE cable connector, IPFE rack connector, or other type of IPFE-compatible connector. Additionally, an IPFE device may be an internal IPFE device integrated into a medical device, while another an IPFE device may be an external IPFE device connected to the medical device via connector, cable, rack, and the like. An IPFE translator may be provided as an interface between an IPFE device and a non-IPFE device (e.g. the host device) to convert IPFE protocol communications and data into the non-IPFE protocol format used by the host device, such as SDC protocol format. Thus, the IPFE translator enables legacy devices and other non-IPFE devices to connect to an IPFE-enabled monitoring or therapy device.

IPFE devices are able to "self-describe" its data by providing metadata. Within a standard framework for physiological parameters and waveforms, an IPFE device is configured to instruct a host device (e.g., a connected medical device) how its data is formatted, how often it is updated, how it should be displayed (e.g., on a monitor display), and how it should be labeled. These items are described by the meta-data that is transmitted by the IPFE device to the host device. IPFE devices may be "plug-and-play" devices. As a result, the host device does not require restart upon being connected to an IPFE device to incorporate the IPFE acquired data. Furthermore, a benefit of the IPFE protocol is that software in an IPFE device can be changed without changing the software in the host device.

Additionally, being that the IPFE communication protocol is modeled on the SDC protocol, IPFE data can be transmitted to other devices within the SDC network. For example, a monitoring or therapy device may receive IPFE data from an IPFE device via the IPFE-compatible connector and may transmit the received IPFE data to another device connected to the SDC network via an SDC communication protocol.

As shown in FIG. 6, the open medical device system 100 in connectable to one or more peripheral devices and systems in the peripheral network 101, including third-party medical devices 102a, current generation patient monitoring (e.g., Infinity®) devices 102b, legacy devices that use MEDIBUS® devices 102c (e.g., medical or therapy devices). These devices are typically patient monitors, which are devices that continuously monitor various parameters of the patient (e.g., ECG signals, heart rate, pulse, end tidal carbon dioxide, and blood pressure, for example) and then display that information to users such as doctors, nurses, EMT (emergency medical technicians), and other medical personnel. Additionally, the peripheral network 101 includes web access systems 102d, patient management systems 102e (e.g., electronic medical records (EMR) system), patient observation systems 102f, messaging and paging systems 102g, legacy systems 102h, and user access systems, also referred to as user interfaces, 102i (e.g., an administrative console) through various communication protocol interfaces. An I/O interface can be an interface for enabling the transfer of information between one or more physiological monitoring devices, and external devices such as peripherals. The I/O interface can be implemented to accommodate various connections and is not limited to, a universal serial bus (USB) connection, parallel connection, a serial connection, coaxial connection, a High-Definition Multimedia Interface (HDMI) connection, or other known connection in the art connecting to external devices.

Various communication protocol interfaces may include an IPFE interface, an SDC interface, a CTAG interface, an RS-232 serial interface (e.g., MEDIBUS®), a serial peripheral interface (SPI), a USB interface, a third-party proprietary protocol-based interface, a data export protocol interface (e.g., an infinity export protocol interface or a legacy export protocol interface), an internet interface, a web interface, a hospital IT (HIT) network interface, a Remote Data Connection (RDC) interface, a server interface, a storage interface, a massaging protocol interface, a paging protocol interface, and the like. It is to be noted that third-party devices (medical and therapy devices) may use the SDC protocol format or non-SDC protocol formats.

The open medical device system 100 may further include a virtual device bridge (VDB) that provides backwards compatibility to Dräger legacy patient monitor devices 102c that use a previous generation protocol (e.g., an Infinity® export protocol). Dräger legacy patient monitoring devices 102c are legacy medical devices that use Infinity® data and communication protocols. As such, the VDB is interposed between Dräger legacy patient monitoring devices and the SDC network of the open medical device system 100.

By way of example, a VDB may maintain a semantic mapping between the two protocols, with one protocol being the SDC protocol. Accordingly, the VDB may include an up-scale converter that up-scales from a previous generation protocol to SDC and a downscale converter that downscales from SDC to the previous generation protocol.

The open medical device system 100 may further include a connectivity converter that translates or converts data output from third-party devices and legacy devices to a common format. More particularly, the connectivity converter a hardware and software component that translates output from legacy Dräger devices and non-SDC speaking third-party devices to the SDC format used in the SDC network of the open medical device system 100.

The connectivity converter translates data in non-SDC protocols formats, such as the MEDIBUS® protocol, a serial protocol, and the like, into the SDC protocol format for use by other components within the open medical device system 100 that use the SDC protocol format.

The software of the connectivity converter contains the latest translation protocols for various system devices and may be periodically updated. These translation protocols make up a driver library stored in memory within the connectivity converter. The connectivity converter includes memory used for buffering for purpose of translation. The software further includes end-to-end encryption that is adapted to the hospital environment that uses the SDC protocol. In this regard, SDC is flexible to allow individual system devices to enter the hospital network, identify themselves, and assess the encryption prior to transmission of information to or from the system.

Any of the devices (e.g., $3^{rd}$ party devices 102a, current devices 102b, legacy devices 102c, user interface 102i, patient management system 102e, patient observation system 102f, messaging and paging system 102g, legacy system 102h, and/or personal computer 54 may implement one or more processors for controlling the general operations of the respective devices. Each one of the one or more processors can be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing device capable of executing any type of instructions, algorithms, or software for controlling the operation and performing the devices.

Figure 7:
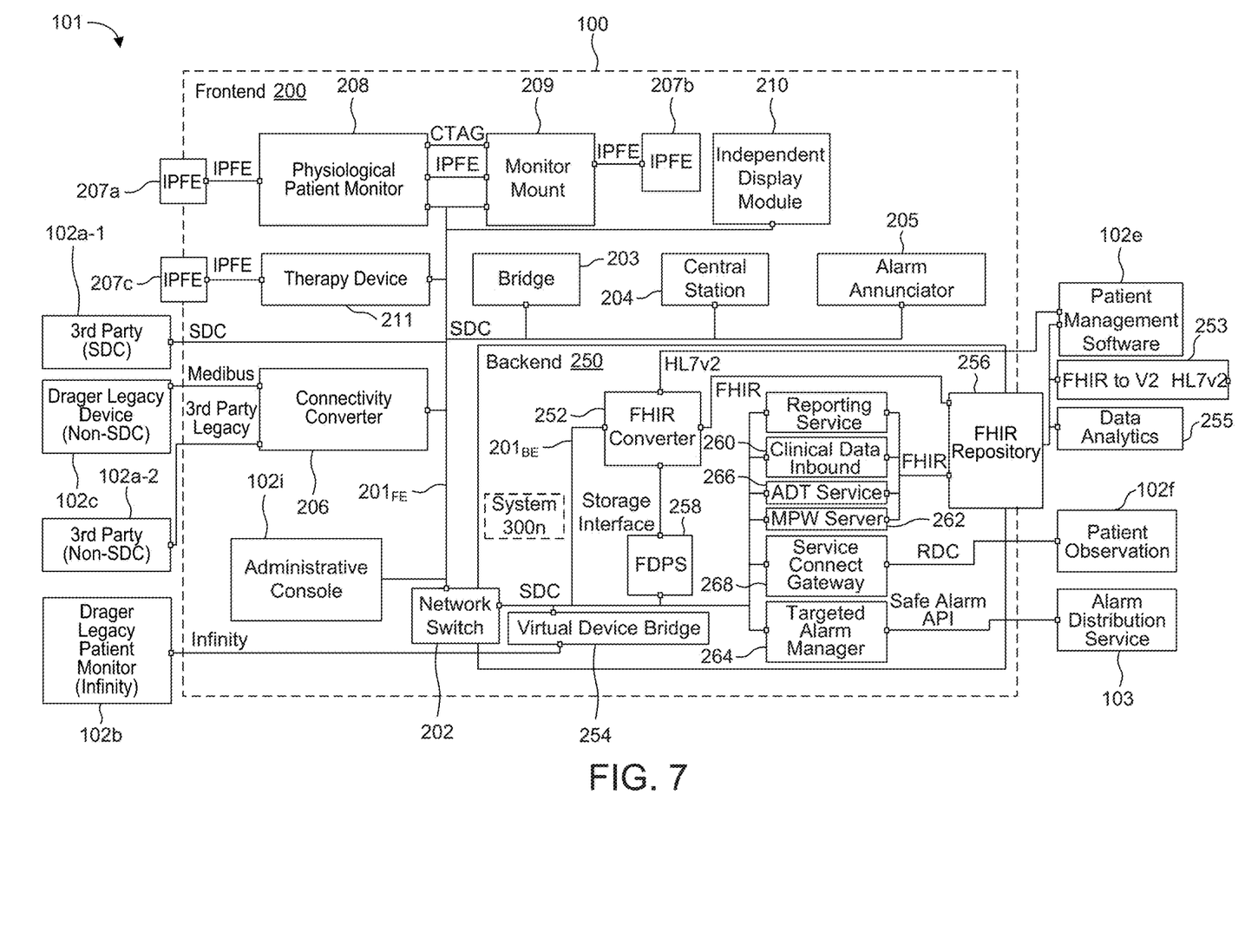
FIG. 7 is a more detailed block diagram illustrating an example of the open medical device system and the peripheral network in which one or more disclosed embodiments may be implemented.

FIG. 7 is a detailed diagram illustrating an example the open medical device system 100 and the peripheral network 101 in which one or more disclosed embodiments may be implemented.

This figure illustrates various peripheral devices and systems that may include elements 102a-102i, described above, that are communicatively coupled to the open medical device system 100 via various protocol interfaces. FIG. 7 further separates third-party devices into two groups, including SDC devices 102a-1 that use the SDC protocol and non-SDC devices 102a-2 that use a non-SDC protocol.

The open medical device system 100 includes a frontend 200 and a backend 250. The frontend 200 includes various PoC medical devices and user equipment, whereas the backend 250 includes various software, network, and storage components deployed, for example, in a datacenter.

Frontend and backend components are connected by various types of communication channels that are differentiated by their communication protocols, with a primary communication network being comprised of a frontend SDC communication network 201FE and a backend SDC communication network 201BE. A network switch 202 connects the frontend SDC communication network 201FE and the backend SDC communication network 201BE and is configured to receive and forward data between the two networks. Other types of secondary communication channels that are differentiated by their communication protocols, including those communication protocols described herein, are connected to one or more components and may interface with the either the frontend SDC communication network 201FE or the backend SDC communication network 201BE by one or more components.

The frontend 200 may include one or more bridges 203 connected to the frontend SDC communication network 201FE. The bridge 203 is configured to access the SDC network, acquire data from other components connected the frontend SDC communication network 201FE and the backend SDC communication network 201BE, and aggregate the acquired data. The accessed data may include, among other accessible data, measurement data, event data, and patient medical record data (e.g., EMR data) corresponding to a patient.

The bridge 203 includes a graphical user interface (GUI) that provides an access point to the acquired and/or aggregated data and may display the acquired and/or aggregated data on a display via the GUI. The bridge 203 may host multiple applications used to acquire and/or aggregate data, and display the data on the display. The bridge 203 can be used to access medical data for multiple patients by manipulating the GUI. Patients can be grouped, for example, by organizational units like departments, locations, caregiver responsibility, or some other criteria. Furthermore, the bridge 203 may be configured monitor for medical events based on the acquired and/or aggregated data and generate alarm signals that trigger audible and/or visual alarms in response to a detected medical event.

The frontend 200 may include a central station 204 connected to the frontend SDC communication network 201FE. The central station 204 generates a workplace aggregation GUI that may be configured to display visual alarms (e.g., those alarms triggered by bridge 203) on a display. The central station 204 may be connected to other devices (e.g., pagers and other mobile devices, such as mobile phones, mobile wristbands, mobile smartwatches, and the like) on the frontend SDC communication network 201FE that are configured to receive alarms from the central station 204. A central station 204 may be provided on each medical ward and perform similar functions described above with respect to the bridge 203.

The frontend 200 may include one or more alarm announcers 205 connected to the frontend SDC communication network 201FE. The alarm announcer 205 may receive alarm signals from the bridge 203, the central station 204 or other device connected to the SDC communication network, and generate audible and/or visual alarms based on the alarm signals. The alarm announcers 205 may be, for example, installed in hallways of a medical facility.

The frontend 200 may include one or more connectivity converters 206 connected to the frontend SDC communication network 201FE. As described above, a connectivity converter 206 is connected to one or more non-SDC devices, such as a Dräger legacy device 102a-2 or a third-party device 102c, and is configured to bi-directionally convert data between non-SDC data formats and SDC data formats. A Dräger legacy device 102a-2 may transmit data in accordance with an RS-232 serial interface (e.g., MEDIBUS®) protocol that is converted into SDC by the connectivity converter 206. Additionally, a third-party, non-SDC device 102a-2 may transmit data in accordance with a third-party protocol (non-SDC protocol) that is converted into SDC by the connectivity converter 206. As a result, the connectivity converter 206 is configured as an interface between non-SDC devices and SDC devices connected to the SDC communication network.

The frontend 200 may include one or more IPFE devices 207a, 207b, and 207c. Each IPFE device 207a, 207b, and 207c is connected via an IPFE communication channel to another device that is connected to the frontend SDC communication network 201FE. Each IPFE device 207a, 207b, and 207c may be removably connected via an IPFE communication channel such that an IPFE device can be connected and disconnected from the network as required for medical care. Each IPFE device 207a, 207b, and 207c includes the algorithms and electronics for measuring physiological metrics of the patient, alarm processing, and settings. An IPFE provides meta-data describing these items so they can be generically used by the connected medical device.

The frontend 200 may include one or more physiological patient monitoring (PPM) devices 208 connected to the frontend SDC communication network 201FE. Each PPM device 208 may be configured to receive physiological data from another device, such as an IPFE device. For example, PPM device 208 may be connected to IPFE device 207a via an IPFE communication channel to receive physiological data therefrom.

The PPM device 208 may also be configured to monitor a patient's physiological data, compare the physiological data to one or more alarm conditions derived from one or more physiological measurement values or value streams, and generate alarm signals that are transmitted within the frontend SDC communication network 201FE should an alarm condition be satisfied. For example, a PPM device may transmit alarm signals to at least one of the bridge 203, the central station 204, or the alarm announcer 205.

The PPM device 208 may be configured to be worn by a patient, may be a hand-held device, may be docked to a lager unit such as a larger PPM device or a console, may be a transportable PPM device, or a stationary PPM device. The PPM device 208 may include a display for displaying physiological measurement values or value streams or traces based on physiological data received from an IPFE device. The PPM device 208 may also display other medically related or patient-related information, for example, received from the SDC network.

Additionally, or alternatively, a PPM device 208 may be portable and configured to be docked (and undocked) to a larger monitoring unit, monitor mount 209, or a console that has or is connected to a display for displaying physiological measurement values, value streams, traces, and/or other medically-related or patient-related information. For example, the frontend 200 may include a monitor mount 209 connected to the to the frontend SDC communication network 201FE. The monitor mount 209 includes a dock with a connector that is configured to engage with a connector of the PPM device 208 (e.g., a male-female connector pair). Accordingly, the monitor mount 209 may provide electro-mechanical-optical mounting such that power is delivered from the monitor mount 209 through the electrical to the PPM device 208 and physiological data is delivered from the PPM device 208 to the monitor mount 209.

The monitor mount 209 may be configured to be coupled to one or more IPFE devices (e.g., IPFE devices 207a and/or 207b) and receive physiological data therefrom. The monitor mount 209 may be coupled to the one or more IPFE devices in conjunction with the PPM device 208. As such, the monitor mount 209 may be configured to aggregate physiological data from multiple sources and display the aggregated physiological data on the display of the mounted PPM device 208. The monitor mount 209 may be configured to transmit physiological data, including aggregated physiological data, to an independent display module 210 via the SDC network in order to display the physiological data thereon.

The frontend 200 may include one or more independent display modules 210 that is connected to the frontend SDC communication network 201FE. An independent display module 210 receive data from one or more SDC clients connected to the SDC communication network and display the received data on its display.

The frontend 200 may include one or more therapy devices 211 devices connected to the frontend SDC communication network 201FE. A therapy device 211 may be a lung ventilator, an anesthesia device, a warming therapy device, or other device that applies a therapy treatment to a patient. Each therapy device 211 is configured to transmit medical data to one or more other devices connected to the SDC network. Additionally, a therapy device 211 may be configured to receive physiological data from another device, such as an IPFE device. For example, therapy device 211 may be connected via an IPFE communication channel to IPFE device 207c to receive physiological data therefrom and apply a therapy treatment based on the received physiological data. The therapy device 211 may also forward the received physiological data and/or therapy data to one or more devices connected to the SDC network.

The frontend system (or simply front end) 200 may include one or more user access systems (or user interfaces) 102i connected to the frontend SDC communication network 201FE. A user access system (or user interface) 102i may be a workstation or console including a computer system, a monitor, and/or at least one user input device (e.g., mouse, keyboard, touchscreen, headset, etc.) that enables a user to access patient information, medically-relevant, and/or administratively-relevant information from the frontend SDC communication network 201FE and the backend SDC communication network 201BE.

The backend 250 may include a VDB 254 connected to the backend SDC communication network 201BE that that provides backwards compatibility to non-SDC devices. Thus, as described above, the VDB 254 may maintain a semantic mapping between the two protocols, with one protocol being the SDC protocol, for exchanging information between devices that use different data protocols.

The backend 250 may include an FHIR converter 252 connected to the backend SDC communication network 201BE. The FHIR converter 252 is configured to receive data in the SDC format and convert the SDC data into an FHIR format and vice versa. The FHIR converter 252 is configured to transmit the FHIR-converted data to one or more FHIR repositories 256 (e.g., a data server) or to transmit SDC-converted data to any endpoint in the frontend SDC communication network 201FE. The FHIR repository 256, for example, may store EMRs of patients and data related to medical personnel. Such data may be requested from one or more devices in the frontend 200. The FHIR repository 256 is further communicatively coupled to the FHIR to V2 HL7v2 module 253 and the data analytics module 255.

The backend 250 may include a full disclosure persistence service (FDPS) 258 connected to the backend SDC communication network 201BE. The FDPS 258 may be a software component couple to memory that is capable of storing all data acquired by the backend SDC communication network 201BE, including data acquired from the frontend SDC communication network 201FE and the VDB 254. The FDPS 258 may store all available data in its raw format, this includes metrics, waveforms, and alerts. The FDPS 258 may be configured to store data for a configured storage duration and remove the data after the configured storage duration has been exceeded or when memory limits have been exceeded. A communication channel between the FHIR converter 252 and the FDPS 258 may be a secure connection if the connect crosses machine boundaries.

The backend 250 may include a clinical data inbound unit 260 connected to the backend SDC communication network 201BE. The clinical data inbound unit 260 is coupled to and between the FHIR repository 256 and the FDPS 258. The clinical data inbound unit 260 is configured to receive messages and reports from other data providers like hospital information systems, such as clinical information systems (CIS), polydimethylsiloxane (PDMS) lab-on-a-chip information systems, lab information systems, rehab information systems, and the like. The clinical data inbound unit 260 may be configured to transmit data to any endpoint (e.g., any SDC client) in the frontend SDC communication network 201FE.

The backend 250 may include an abstract data type (ADT) service unit 266 connected to the backend SDC communication network 201BE. The ADT service unit 266 is coupled to and between the FHIR repository 256 and the FDPS 258. The ADT service unit 266 is configured to acquire ADT data from an EMR via the FHIR repository and provide the ADT data to the SDC network. The ADT data can be made available to an SDC client on the frontend SDC communication network 201FE. The ADT service unit 266 may use the FHIR converter 252 as an inbound interface.

The backend 250 may include a mobile patient watch server 262 connected to the backend SDC communication network 201BE. The mobile patient watch server 262 is coupled to and between the FHIR repository 256 and the FDPS 258. The mobile patient watch server 262 may enable thin client access to device data for mobile use and thus may be a web server with access to the FHIR repository 256.

The backend 250 may include a service connect gateway 268 connected to the backend SDC communication network 201BE. The service connect gateway 268 may interface to medical devices via a remote data connection (RDC). In particular, the service connect gateway 268 may communicate with a patient observation system 102*f* that provides remote medical data acquired by one or more remote medical devices.

The backend 250 may include an alarm managing unit 264 connected to the backend SDC communication network 201BE. The alarm managing unit 264 serves as an interfacing component from the internal SDC network to an external alarm distribution service 103.

Further, any, all, or some of the computing devices in the physiological monitoring device may be adapted to execute any operating system, including Linux, UNIX, Windows Server, etc., as well as virtual machines adapted to virtualize execution of a particular operating system, including customized and proprietary operating systems. The physiological monitoring device are further equipped with components to facilitate communication with other computing devices over one or more network connections, which may include connections to local and wide area networks, wireless and wired networks, public and private networks, and any other communication network enabling communication in the system.

A communications interface of each of the respective devices may allow the physiological monitoring device to directly or indirectly to communicate with one or more computing networks and devices. The communications interface can include various network cards, interfaces or circuitry to enable wired and wireless communications with such computing networks and devices. The communications interface can also be used to implement, for example, a Bluetooth connection, a cellular network connection, and/or a Wi-Fi connection. Other wireless communication connections implemented using the communications interface include wireless connections that operate in accordance with, but are not limited to, IEEE802.11 protocol, a Radio Frequency For Consumer Electronics (RF4CE) protocol, ZigBee protocol, and/or IEEE802.15.4 protocol. Other wireless communication connections implemented using the communications interface include wireless connections that operate in accordance with, but are not limited to, IEEE802.11 protocol, a Radio Frequency For Consumer Electronics (RF4CE) protocol, ZigBee protocol, and/or IEEE802.15.4 protocol.

It is further to be noted that methods disclosed in the specification or in the claims may be implemented by a device having means for performing each of the respective acts of these methods.

Lastly, it is to be understood that the disclosure of multiple acts or functions disclosed in the specification or claims may not be construed as to be within the specific order. Therefore, the disclosure of multiple acts or functions will not limit these to a particular order unless such acts or functions are not interchangeable for technical reasons. Furthermore, in some embodiments a single act may include or may be broken into multiple sub acts. Such sub acts may be included and part of the disclosure of this single act unless explicitly excluded.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application-specific integrated circuits (ASICs), field programmable logic arrays (FPGAs), programmable logic controller (PLC), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure. A control unit may use electrical signals and digital algorithms to perform its receptive, analytic, and control functions, which may further include corrective functions. Such hardware, software, and firmware may be implemented within the same device or within separate devices to support the various techniques described in this disclosure.

One or more aspects of the present disclosure may be implemented as a non-transitory computer-readable recording medium having recorded thereon a program embodying methods/algorithms for instructing the processor to perform the methods/algorithms. Thus, a non-transitory computer-readable recording medium may have electronically readable control signals stored thereon, which cooperate (or are capable of cooperating) with a programmable computer system such that the respective methods/algorithms are performed. The non-transitory computer-readable recording medium can be, for example, a CD-ROM, DVD, Blu-ray disc, a RAM, a ROM, a PROM, an EPROM, an EEPROM, a FLASH memory, or an electronic memory device.

Although various embodiments have been disclosed, it will be apparent to those skilled in the art that various changes and modifications can be made which will achieve some of the advantages of the concepts disclosed herein without departing from the spirit and scope of the invention. It will be obvious to those reasonably skilled in the art that other components performing the same functions may be suitably substituted. It is to be understood that other embodiments may be utilized and structural or logical changes may be made without departing from the scope of the present invention. It should be mentioned that features explained with reference to a specific figure may be combined with features of other figures, even in those not explicitly mentioned. Such modifications to the general inventive concept are intended to be covered by the appended claims and their legal equivalents.

What is claimed is:

1. A system configured for sampling and analyzing common mode noise on electrocardiogram signals to help to minimize interference to the electrocardiogram signals, the system comprising:
   one or more hardware processors configured by machine-readable instructions to:
      obtain electrocardiogram signals from one or more sensors configured to be attached to a patient and communicatively connected to a patient monitor;
      receive the electrocardiogram signals from one or more sensors by the patient monitor;
      display the electrocardiogram signals on one or more displays of the patient monitor;
      sample and analyze a direct current range and an alternating current spectrum using spectrum analysis to identify common mode interference levels in the obtained electrocardiogram signals;
      display the direct current range and the alternating current spectrum via the one or more displays of the patient monitor; and
      update the display of the direct current range and the alternating current spectrum in real time to help to identify sources of common mode interference.

2. The system of claim 1, wherein users make changes to at least one of system configurations and system location in order to cause changes in amounts of common interference detected by the patient monitor.

3. The system of claim 2, wherein the changes in the amounts of common mode interference are reflected in direct current range and the alternating current spectrum.

4. The system of claim 2, wherein the changes in the amounts of common mode interference are indicative of causes of the common mode noise.

5. The system of claim 4, wherein identifying causes of common mode interference further comprises generating and storing a knowledge base of interference causes.

6. The system of claim 5, wherein the knowledge base of interference causes is stored in a database so that new interference measurements can be compared to measurements of previous interference causes.

7. The system of claim 1, wherein the sampling and analyzing a direct current range and an alternating current spectrum to identify common mode interference levels includes fast Fourier transformation-based spectrum analysis.

8. The system of claim 1, wherein a measurement at a right leg drive output provides an overall common mode noise experienced by the patient monitor.

9. The system of claim 1, wherein the one or more hardware processors are further configured by machine-readable instructions to identify sources of common mode interference.

10. The system of claim 1, wherein updating the display comprises dynamically displaying in real-time the common mode noise spectrum in response to the various common mode noise being measured.

11. A computing platform configured for sampling and analyzing electrocardiogram signals to enable filtering of common mode interference of the electrocardiogram signals, the computing platform comprising:
    a non-transient computer-readable storage medium having executable instructions embodied thereon; and
    one or more hardware processors configured to execute the instructions to:
       obtain electrocardiogram signals from one or more sensors configured to be attached to a patient and communicatively connected to a patient monitor;
       receive the electrocardiogram signals from one or more sensors by the patient monitor;
       display the electrocardiogram signals on one or more displays of the patient monitor;
       sample and analyze a direct current range and an alternating current spectrum using spectrum analysis to identify common mode interference levels in the obtained electrocardiogram signals;
       display the direct current range and the alternating current spectrum via the one or more displays of the patient monitor; and
       update the display of the direct current range and the alternating current spectrum in real time to identify sources of common mode interference.

12. The computing platform of claim 11, wherein users make changes to at least one of system configurations and system location in order to cause changes in amounts of common interference detected by the patient monitor.

13. The computing platform of claim 12, wherein the changes in the amounts of common mode interference are reflected in direct current range and the alternating current spectrum.

14. The computing platform of claim 12, wherein the changes in the amounts of common mode interference are indicative of causes of the common mode interference.

15. The computing platform of claim 14, wherein identifying causes of common mode interference further comprises generating and storing a knowledge base of interference causes.

16. The computing platform of claim 15, wherein the knowledge base of interference causes is stored in a database so that new interference measurements can be compared to measurements of previous interference causes.

17. The computing platform of claim 11, wherein sampling and analyzing a direct current range and an alternating current spectrum to identify common mode interference levels includes fast Fourier transformation-based spectrum analysis.

18. The computing platform of claim 11, wherein a measurement at a right leg drive output provides an overall common mode noise experienced by the patient monitor.

19. The computing platform of claim 11, wherein the one or more hardware processors are further configured to execute the instructions to identify sources of common mode interference.

20. The computing platform of claim 11, wherein updating the display comprises dynamically displaying in real-time the common mode noise spectrum in response to the various common mode noise being measured.

21. A method for sampling and analyzing electrocardiogram signals to enable filtering of common mode interference of the electrocardiogram signals, the method comprising:
obtaining electrocardiogram signals from one or more sensors configured to be attached to a patient and communicatively connected to a patient monitor;
receiving the electrocardiogram signals from one or more sensors by the patient monitor;
displaying the electrocardiogram signals on one or more displays of the patient monitor;
sampling and analyzing a direct current range and an alternating current spectrum using spectrum analysis to identify common mode interference levels in the obtained electrocardiogram signals;
displaying the direct current range and the alternating current spectrum via the one or more displays of the patient monitor; and
updating the display of the direct current range and the alternating current spectrum in real time to identify sources of common mode interference.

22. The method of claim 21, wherein users make changes to at least one of system configurations and system location in order to cause changes in amounts of common interference detected by the patient monitor.

23. The method of claim 22, wherein the changes in the amounts of common mode interference are reflected in direct current range and the alternating current spectrum.

24. The method of claim 22, wherein the changes in the amounts of common mode interference are indicative of causes of the common mode interference.

25. The method of claim 24, wherein identifying causes of common mode noise further comprises generating and storing a knowledge base of interference causes.

26. The method of claim 25, wherein the knowledge base of interference causes is stored in a database so that new interference measurements can be compared to measurements of previous interference causes.

27. The method of claim 21, wherein a measurement at a right leg drive output provides an overall common mode interference experienced by the patient monitor.

28. The method of claim 21, further comprising identifying sources of common mode interference.

29. The method of claim 21, wherein updating the display comprises dynamically displaying in real-time the common mode noise spectrum in response to the various common mode noise being measured.

* * * * *